United States Patent [19]

Tanaka et al.

[11] 4,106,942

[45] Aug. 15, 1978

[54] SILVER HALIDE EMULSION CONTAINING YELLOW COLOR COUPLERS

[75] Inventors: Mitsugu Tanaka; Kiyoshin Nakazyo, 01, Shiba; Keisuke; Atsuaki Arai, all of Kanagawa, Japan

[73] Assignee: Fuji Photo Film Co., Ltd., Minami Ashigara, Japan

[21] Appl. No.: 791,084

[22] Filed: Apr. 26, 1977

Related U.S. Application Data

[63] Continuation of Ser. No. 564,565, Apr. 2, 1975, abandoned.

[30] Foreign Application Priority Data

Apr. 2, 1974 [JP] Japan .................................. 49-37239

[51] Int. Cl.$^2$ .............................................. G03C 1/40
[52] U.S. Cl. ..................... 96/100 N; 96/22; 96/55; 96/74; 96/100 R; 260/562 R
[58] Field of Search .................... 96/55, 100 R, 100 N

[56] References Cited

U.S. PATENT DOCUMENTS

| 3,408,194 | 10/1968 | Loria ....................................... 96/100 |
| 3,580,721 | 5/1971 | Iwama et al. ........................... 96/100 |
| 3,619,190 | 11/1971 | Verbrugghe et al. .................... 96/55 |
| 3,770,446 | 11/1973 | Sato et al. ............................... 96/100 |
| 4,029,508 | 6/1977 | Tanaka et al. .......................... 96/100 |

*Primary Examiner*—J. Travis Brown
*Attorney, Agent, or Firm*—Sughrue, Rothwell, Mion, Zinn and Macpeak

[57] ABSTRACT

A yellow color forming photographic coupler represented by the following general formula (I)

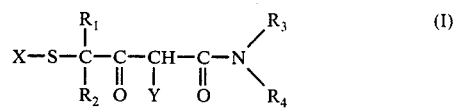

in which X represents an aliphatic group, an aromatic group or a heterocyclic group; Y represents a hydrogen atom or a coupling off group; $R_1$ and $R_2$ each represents an aliphatic group, or $R_1$ and $R_2$ can combine to form a ring; and $R_3$ and $R_4$ each represents a hydrogen atom, an aliphatic group, an aromatic group or a heterocyclic group.

9 Claims, No Drawings

SILVER HALIDE EMULSION CONTAINING YELLOW COLOR COUPLERS

This is a continuation, of application Ser. No. 564,565, filed Apr. 2, 1975, now abandoned.

BACKGROUND OF THE INVENTION

1. Field of the Invention

The present invention relates to a photographic coupler, and more particularly to a novel yellow color forming coupler which is suitable for use in the formation of color photographic images.

2. Description of the Prior Art

In the formation of color photographic images by a subtractive color reproduction process, an aromatic primary amine compound, especially a N,N-disubstituted para-phenylenediamine compound, is used as a developing agent, to reduce the silver halide grains in an exposed photographic emulsion layer, and the concurrently produced oxidation product of the developing agent is coupled with the color forming coupler to form a cyan, magenta or yellow image dye.

Couplers for use in the color developing process are compounds which have a phenolic hydroxy group, an anilinic amino group or an active methylene group, and, by coupling with the oxidation product of the aromatic primary amine developing agent form dyes which absorb light in the visible wave length range.

The yellow dye images exhibit a specific absorption to blue light in the wave length region ranging from about 400 to 500 millimicrons. Previously known yellow color forming couplers include β-ketoacetoacetic esters, β-diketones, N,N-malonic diamides and α-acylacetamides, and the like.

Of these compounds, pivaloyl acetanilide type compounds as described in U.S. Pat. No. 3,265,506 are widely used, as yellow color forming couplers, in the field of color photography. Although this series of couplers has many preferred properties, they also have a number of disadvantages and are by no means completely satisfactory. For instance, these couplers generally have poor coupling reactivity, the dyes which are formed from these couplers upon color development with certain useful color developing agents have poor fastness to light, and the leuco dyes formed upon color development are highly stable and further oxidation of the leuco dyes to form the dye by treatment in a strong oxidizing bath is necessary.

Also α-phenoxy-iso-butyryl acetanilide type couplers as described in German Patent Application OLS No. 1,956,281 and U.S. Pat. No. 3,770,446 are not satisfactory. These couplers have the disadvantages in that the dyes formed from these couplers have an absorption maximum in a relatively short wave length range and have a broad absorption into a longer wave length range, resulting in poor color reproduction, in that the preparation of the corresponding β-ketoesters which are the starting materials of the couplers includes difficult procedures and the yields are poor, and the like.

SUMMARY OF THE INVENTION

An object of the present invention is to provide a novel yellow color forming coupler suitable for use in color photography by a subtractive color process.

Another object of the present invention is to provide a novel yellow color forming coupler which has a high coupling reactivity and the dye formation can be completed in a color developer solution.

Another object of the present invention is to provide a novel yellow color forming coupler which forms a dye having excellent spectral absorption properties and light fastness.

Still another object of the present invention is to provide a novel yellow color forming coupler which can be prepared in a simple procedure and in a high yield.

A further object of the present invention is to provide a method of forming a dye image by developing a silver halide emulsion in the presence of a novel yellow color forming coupler.

A further object of the present invention is to provide a color photographic light-sensitive material having a silver halide emulsion containing a novel yellow color forming coupler.

A still further object of the present invention is to provide a color developer solution containing a novel yellow color forming coupler.

An even further object of the present invention is to provide a yellow dye image having suitable spectral absorption properties for color reproduction by a subtractive color process and excellent light fastness.

These and other objects of the present invention will become apparent from the following detailed description.

These objects of the present invention are accomplished by a yellow color forming coupler represented by the following general formula (I)

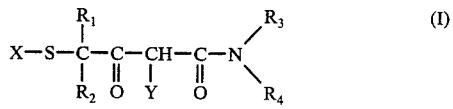

in which X represents an aliphatic group, an aromatic group or a heterocyclic group; Y represents a hydrogen atom or a group capable of being released on coupling with the oxidation product of a primary aromatic amine developing agent; $R_1$ and $R_2$, which can be the same or different, each represents an aliphatic group or $R_1$ and $R_2$ can combine to form a ring; and $R_3$ and $R_4$, which can be the same or different, each represents a hydrogen atom, an aliphatic group, an aromatic group or a heterocyclic group.

DETAILED DESCRIPTION OF THE INVENTION

In the above-described general formula (I), suitable groups represented by X include aliphatic groups having 1 to 40 carbon atoms, aromatic groups having 6 to 40 carbon atoms and heterocyclic groups having 3 to 40 carbon atoms.

Suitable examples of Y include groups connected to the coupling position of the coupler with a nitrogen atom, an oxygen atom or a sulfur atom, and also Y can be a hydrogen atom and a halogen atom.

Suitable groups represented by $R_1$ and $R_2$ include groups having 1 to 10 carbon atoms, respectively. Also suitable groups represented by $R_3$ and $R_4$ include aliphatic groups having 1 to 40 carbon atoms, aromatic groups having 6 to 40 carbon atoms and heterocyclic groups having 3 to 40 carbon atoms.

In greater detail, the aliphatic group represented by X in the general formula (I) includes an alkyl group. The alkyl group can be in the form of a straight chain, a branched chain or a ring and preferably can have 1 to 20 carbon atoms. The alkyl group can be substituted with one or more alkoxy groups such as methoxy, ethoxy, methoxyethoxy, octoxy and like groups, aryl groups such as phenyl, tolyl, naphthyl and like groups, heterocyclic groups such as imidazolyl, furyl, pyridyl and like groups, aryloxy groups such as phenoxy, tolyloxy and like groups, acyl groups such as acetyl, benzoyl and like groups, acrylamino groups such as acetamide, butyramido, benzamido and like groups, hydroxy groups, halogen atoms such as chloride, bromine, etc., and the like. The aromatic group and the heterocyclic group represented by X include a phenyl group, a naphthyl group, a pyridyl group, a furyl group, and the like and can be substituted with one or more alkyl groups, such as methyl, ethyl, tert-butyl, octyl, octadecyl and like groups, alkoxy groups such as methoxy, ethoxy, methoxyethoxy, octoxy and like groups, aryl groups such as phenyl, tolyl, naphthyl and like groups, aryloxy groups such as phenoxy, tolyloxy and like groups, acyl groups such as acetyl, benzoyl and like groups, acylamino groups such as acetamido, butyramido, benzamido and like groups, hydroxy groups, halogen atoms such as chlorine, bromine, etc., and the like.

The coupling off group other than a hydrogen atom and a halogen atom represented by Y suitably includes an acyloxy group (particularly, an alkylacyloxy group having 2 to 20 carbon atoms, an arylacyloxy group having 7 to 30 carbon atoms) as described in U.S. Pat. No. 3,447,928, a phenoxy group (particularly, a phenoxy group substituted with an electron attractive group) as described in U.S. Pat. No. 3,408,194, a sulfoxy group (particularly, an alkylsulfoxy group having 1 to 20 carbon atoms, an arylsulfoxy group having 6 to 25 carbon atoms) as described in U.S. Pat. No. 3,415,652, a group having a sulfimide structure as described in U.S. Pat. No. 3,730,722, a thiocyano group as described in U.S. Pat. No. 3,253,924, a group having an imide type structure (particularly, a succinimido group, a phthalimido group, a hydantoin group, an oxazolidine-dione group, a derivative thereof) as described in U.S patent application Ser. No. 235,937, filed Mar. 20, 1972, U.S. patent application Ser. No. 319,806, filed Dec. 29, 1972 and U.S. patent application Ser. No. 395,873, filed Sep. 10, 1973, a group containing a sulfur atom (particularly, a mercaptotetrazole group and a derivative thereof, a thiophenol group and a derivative thereof) as described in U.S. Pat. No. 3,227,554 and British Pat. No. 1,224,555, a group having an azo group (particularly, a phenylazo group and a derivative thereof) as described in U.S. Pat. No. 3,148,062, a group having a triazole structure (particularly, a benzotriazole group and a derivative thereof) as described in U.S. Pat. No. 3,617,291 and U.S. patent application Ser. No. 454,525 filed Mar. 25, 1974, a group having a pyrazole structure as described in German patent application OLS No. 2,163,811, and the like.

The aliphatic groups represented by $R_1$ and $R_2$ include an alkyl group. The alkyl group can be in the form of a straight chain or a branched chain and can have 1 to 6 carbon atoms. The alkyl group can be substituted with one or more alkoxy groups, aryl groups, aryloxy groups, and the like. Also $R_1$ and $R_2$ can combine to form a ring.

The aliphatic groups represented by $R_3$ and $R_4$ include an alkyl group. The alkyl group can be in the form of a straight chain, a branched chain or a ring and can have 1 to 20 carbon atoms. The alkyl group can be substituted with one or more alkoxy groups, aryl groups, aryloxy groups, and the like.

The aromatic groups represented $R_3$ and $R_4$ include a substituted or unsubstituted phenyl group. Suitable substituents can be a monovalent substituent such as a halogen atom, a nitro group, a cyano group, a thiocyano group, a hydroxy group, an alkoxy group, an aryloxy group, an alkyl group, an alkenyl group, an aryl group, an amino group, a carboxy group, an acyl group, an alkoxycarbonyl group, an aryloxycarbonyl group, a carbamoyl group, an acylamino group, a sulfo group, an alkylsulfonyl group, an arylsulfonyl group, an alkoxysulfonyl group, an aryloxysulfonyl group, a sulfamoyl group, a sulfonamido group, and the like, and further a divalent substituent which can form a condensed ring together with the phenyl group. Examples of condensed rings formed by phenyl groups having such a divalent substituent are a naphthyl group, a quinolyl group, an isoquinolyl group, a chromanyl group, a coumaranyl group, a tetrahydronaphthyl group, and the like. These monovalent and divalent substituents can, in turn, have additional substituents.

The heterocyclic groups represented by $R_3$ and $R_4$ are connected to the coupler residue through a carbon atom which forms the heterocyclic ring and is one of the members constituting the conjugated electron system of the ring. These heterocyclic groups include those of the thiophene series (for example, 2-thienyl, 3-thienyl, 2-benzothienyl, 3-benzothienyl, 2-naphthothienyl, 3-naphthothienyl, etc.), the furan series (for example, 2-furyl, 3-furyl, 2-benzofuranyl, 3-benzofuranyl, 1-isobenzofuranyl, 3-isobenzofuranyl, etc.), the pyran series (for example, 3-pyranyl, 4-pyranyl, 5-pyranyl, 6-pyranyl, etc.), the chromene series (for example, 3-chromenyl, 4-chromenyl, etc.), the pyrrole series (for example, 2-pyrrole, 1-methyl-3-pyrrole, etc.), the pyrazole series (for example, 4-pyrazolyl, 1-phenyl-3-pyrazolyl, etc.), the pyridine series (for example, 2-pyridyl, 3-pyridyl, 4-pyridyl, 2-quinolyl, 3-quinolyl, 4-quinolyl, 1-isoquinolyl, 3-isoquinolyl, 4-isoquinolyl, etc.), the pyrazine series (for example, 2-pyrazinyl, 2-quinoxalinyl, etc.), the pyrimidine series (for example, 2-pyrimidinyl, 4-pyrimidinyl, 5-pyrimidinyl, 2-quinazolinyl, 4-quinazolinyl, etc.), the pyridazine series (for example, 3-pyridazinyl, 4-pyridazinyl, 3-cinnolinyl, 4-cinnolinyl, etc.), the indolizine series (for example, 1-indolizinyl, 2-indolizinyl, 3-indolizinyl, 5-indolizinyl, 6-indolizinyl, 7-indolizinyl, etc.), the perimidine series (for example, 2-perimidinyl, etc.), the thiazole series (for example, 2-thiazolyl, 2-benzothiazolyl, 3-isothiazolyl, 4-isothiazolyl, 5-isothiazolyl, etc.), the imidazole series (for example 2-benzoimidazolyl, etc.), the oxazole series (for example, oxazolyl, 4-oxazolyl, etc.), the 1,3,5-triazine series (for example, 1,3,5-triazinyl, etc.), the oxazine series, and the like.

These heterocyclic groups can be substituted with one or more of a halogen atom, a nitro group, a cyano group, a thiocyano group, a hydroxy group, an alkoxy group, an aryloxy group, an alkyl group, an alkenyl group, an aryl group, an amino group, a carboxy group, an acyl group, an alkoxycarbonyl group, an aryloxycarbonyl group, a carbamoyl group, an acylamino group, a sulfo group, an alkylsulfonyl group, an arylsulfonyl group, an alkoxysulfonyl group, an aryloxysulfonyl, a sulfamoyl group, a sulfonamido group, and the like.

Of the yellow color forming couplers included in the above-describe general formula (I), compounds in which either $R_3$ or $R_4$ is a phenyl group in which one of the ortho positions is substituted with a halogen atom such as a fluorine atom, a chlorine atom, a bromine atom, etc., an alkoxy group such as a methoxy group, an ethoxy group, a propoxy group, an octoxy group, etc., an aryloxy group such as a phenoxy group, a tolyloxy group, etc., an alkyl group such as a methyl group, an ethyl group, a butyl group, etc., or an amino group such as an N,N-dimethylamino group, an N-n-butyl-N-n-octylamino group, etc. are preferred. Furthermore, by substituting the meta position, the para position or both the meta and para positions of the phenyl group represented by $R_3$ or $R_4$ with the above-described monovalent substituent, the properties of the coupler per se and the dye formed therefrom can be varied to adapt to purposes of use.

Of the yellow color forming couplers which can be used in the present invention, particularly preferred compounds are those represented by the following general formula (II)

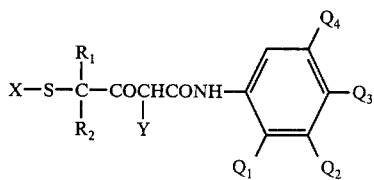

in which X, Y, $R_1$ and $R_2$ are the same as defined in the general formula (I); $Q_1$ represents a halogen atom (for example, fluorine, chlorine, bromine, etc.), an alkyl group (for example, methyl, ethyl, tert-butyl, etc.), an alkoxy group (for example, methoxy, ethoxy, propoxy, octoxy, etc.), an aryloxy group (for example, phenoxy, methylphenoxy, etc.), or an N-substituted amino group (for example, N,N-dimethylamino, N-butyl-N-octylamino etc.), $Q_2$, $Q_3$ and $Q_4$, which may be the same or different, each represents a hydrogen atom, a halogen atom (for example, fluorine, chlorine, bromine, etc.), an alkyl group (for example, methyl, ethyl, amyl, octadecyl, etc.), an alkoxy group (for example, methoxy, ethoxy, dodecyloxy, etc.), an aryl group (for example, phenyl, methylphenyl, etc.), an aryloxy group (for example, phenoxy, methylphenoxy, etc.), an alkoxycarbonyl group (for example, ethoxycarbonyl, hexadecyloxycarbonyl, etc.), a carbamoyl group (for example, methylcarbamoyl, dodecylcarbamoyl, N-ω-(2,4-di-tert-amylphenoxy)butylcarbamoyl, etc.), a sulfamoyl group (for example, methylsulfamoyl, diethylsulfamoyl, N-γ-(2,4-di-tert-amylphenoxy)propylsulfamoyl, etc.), an alkylamino group (for example, ethylamino, N-N-dimethylamino, etc.), an arylamino group (for example, anilino, etc.), a sulfonamino group (for example, methylsulfonamino, α-(3-pentadecylphenoxy)propylsulfonamino, etc.), an acylamino group (for example, acetamido, α-(3-pentadecylphenoxy)butyramido, etc.), a carboxy group, a sulfo group, a cyano group, or a hydroxy group.

Methods of forming yellow color images using the photographic couplers of the present invention include an embodiment in which the yellow forming couplers are present in a photographic emulsion layer, and an embodiment in which the yellow color forming couplers are present in a color developer solution. The former is designated a coupler-in-the-emulsion type, and in which the couplers are usually incorporated in an emulsion layer during the manufacture of the photographic light-sensitive materials. The latter is designated a coupler-in-the-developer type, and in which the couplers are usually dissolved in a color developer solution and diffuse into an emulsion layer during the color development.

Couplers which can be used in the coupler-in-the-emulsion type preferably are fixed in a specific emulsion layer. That is, these couplers must be diffusion resistant. Otherwise these couplers migrate in the photographic light-sensitive material and form dyes in other emulsion layers of different spectral sensitivity resulting in a marked reduction in the color reproducibility of the photographic materials.

In order to render the couplers diffusion resistant, a group containing a hydrophobic group having at least 8, preferably up to about 32, carbon atoms is preferably introduced into the coupler molecule. Such groups are conventionally designated ballasting groups. The ballasting group can be connected to the coupler skeleton either directly or through an amino bond, an ether bond, a thioether bond, a carbonamido bond, a sulfonamido bond, an ureido bond, an ester bond, an imido bond, a carbonyl bond, a carbamoyl bond, a sulfamoyl bond, a sulfonyl bond, or the like.

In the yellow color forming couplers of the present invention, any of the known ballasting groups can be used. Many ballasting groups are known as described in U.S. Pat. Nos. 2,600,788, 2,865,751, 3,337,344 and 3,418,129, Japanese patent publication Nos. 27563/1964 and 19035/1970, Japanese patent application Nos. 35379/1973 and 69383/1973, etc., and these can be advantageously employed in the photographic couplers of the present invention.

Typical hydrophobic groups include an alkyl group, an alkenyl group, an alkoxyalkyl group, an alkyl-substituted aryl group, an alkoxy-substituted aryl group, a terphenyl group, and the like, and these groups can be substituted with a halogen atom such as fluorine, chlorine, etc., a nitro group, a cyano group, an alkoxycarbonyl group, an amido group, a carbamoyl group, a sulfonamido group, and the like.

Specific examples of ballasting groups which are suitable are as follows.

(I) Alkyl groups and alkenyl groups, such as; —CH$_2$—CH(C$_2$H$_5$)$_2$,

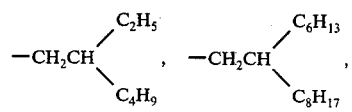

—C$_{12}$H$_{25}$, —C$_{16}$H$_{33}$, C$_{17}$H$_{33}$ (II) Alkoxyalkyl groups such as; —(CH$_2$)$_3$—O—(CH$_2$)$_7$CH$_3$,

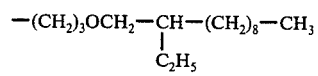

as described in Japanese patent publication No. 27536/64

(III) Alkylaryl groups such as;

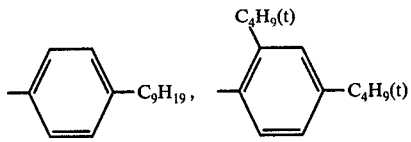

(IV) Alkylaryloxyalkyl groups such as;

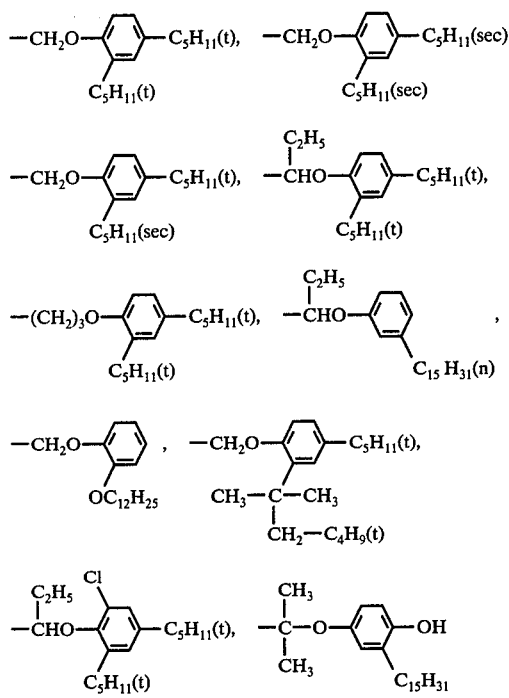

(V) Acylaminoalkyl groups such as;

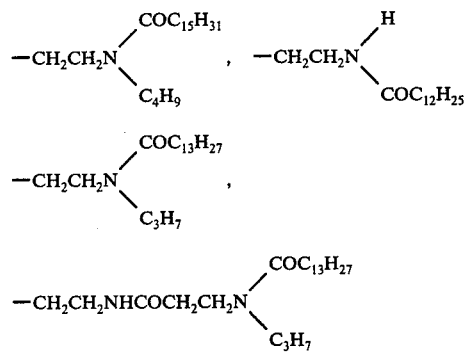

as described in U.S. Pat. Nos. 3,333,344 and 3,418,129

(VI) Alkoxyaryl groups and aryloxyaryl groups such as;

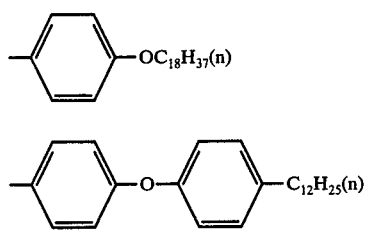

(VII) Residues having a long-chain aliphatic, alkyl or alkenyl group and a water-solubilizing carboxy or sulfo group, such as;

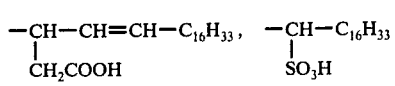

(VIII) Ester-substituted alkyl groups such as;

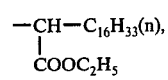

(IX) Aryl- or heterocyclic ring-substituted alkyl groups such as;

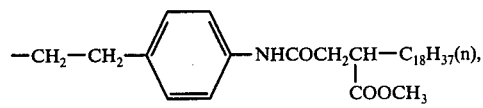

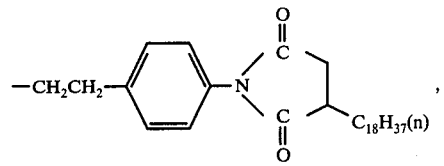

(X) Aryloxyalkylcarbonyl-substituted aryl groups such as;

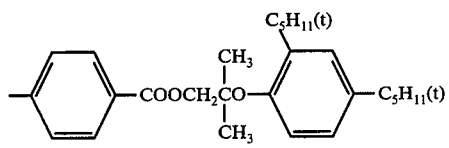

A coupler having diffusion resistant group in the molecule can be dissolved in an organic solvent and incorporated into an photographic emulsion as fine particles in a conventional manner. An example of a method of dispersing the couplers which is particularly suitable in the practice of the present invention is described in detail in U.S. Pat. No. 3,676,137. Organic solvents which can be used to dissolve the coupler are described in U.S. Pat. Nos. 2,322,027, 3,253,291, 3,574,627, etc. These solvents include those which are sparingly soluble in water and have a high boiling point (higher than about 170° C) and remain in a color photographic light-sensitive material together with the couplers, for example, substituted hydrocarbons, carboxylic acid esters, carboxylic acid amides, phosphoric acid esters, ethers, and the like. Specific examples of these solvents are di-n-butyl phthalate, di-isooctyl azelate, di-n-butyl sebacate, tricresyl phosphate, tri-n-hexyl phosphate, N,N-diethylcaprylamide, butyl-m-pentadecylphenylether, chlorinated paraffin, and the like. An auxiliary solvent which can be removed during the production of the photographic light-sensitive material can be advantageously used in combination with the high boiling solvent to facilitate the dissolution of the coupler. Examples of such solvents are propylene carbonate, ethyl acetate, butyl acetate, cyclohexanol, tetrahydrofuran, cyclohexanone, and the like.

The facilitate the formation of a fine dispersion of the oil-soluble couplers into a hydrophilic high molecular weight substance which is used in a photographic emulsion, a surface active agent is advantageously used. Particularly, an anionic surface active agent such as sodium cetylsulfate, sodium p-dodecylbenzene sulfonate, sodium nonylnaphthalene sulfonate, sodium di-(2-ethylhexyl)-α-sulfosuccinate, and the like, and a non-ionic surface active agent such as sorbitan sesquioleate, sorbitan monolaurate, and the like are suitable. An emulsifying device such as a homogenizer, a colloid mill, an ultrasonic wave emulsifier, and the like is preferably used to prepare a dispersion of an oil-soluble coupler.

The diffusion resistant coupler which has both a ballasting group and a carboxylic acid group or a sulfonic acid group is soluble in an neutral or weakly alkaline aqueous solution. By addition of an aqueous solution of the coupler to a photographic emulsion, the coupler can be incorporated into the photographic emulsion. It is believed that the coupler is rendered diffusion resistant in a micellar form in the hydrophilic high molecular weight substance.

A diffusible coupler which does not have a diffusion resistant group can be used by addition to a color developer solution containing an aromatic primary amine color developing agent.

Representative examples of yellow color forming couplers represented by the general formula (I) are illustrated below.

(1) 2′-Chloro-5′-[2-(2,4-di-tert-amylphenoxy)-butyramido]-(2-ethylthio-2-methylpropionyl)acetanilide
(2) 2′-Chloro-5′-[4-(2,4-di-tert-amylphenoxy)-butyramido]-(2-ethylthio-2-methylpropionyl)acetanilide
(3) 2′-Chloro-(2-n-nonylthio-2-methylpropionyl)acetanilide
(4) 2′-Methoxy-(2-n-octadecylthio-2-methylpropionyl)-acetanilide
(5) N-(2-Pyridyl)-(2-ethylthio-2-methylpropionyl)-acetamide
(6) 4′-Chloro-(2-ethylthio-2-methylpropionyl)acetanilide
(7) 2′-Methoxy-5′-nitro-(2-ethylthio-2-methylpropionyl)-acetanilide
(8) 2′-Chloro-5′-n-dodecanesulfonamido-(2-cyclohexythio-2-methylpropionyl)acetanilide
(9) 2′-Chloro-5′-n-dodecyloxycarbonyl-(2-ethylthio-2-methylpropionyl)acetanilide
(10) 2′-n-Octadecyloxy-(2-ethylthio-2-methylpropionyl)-acetanilide
(11) 2′-Methoxy-5′-[4-(2,4-di-tert-amylphenoxy)-butyramido]-(2-ethylthio-2-methylpropionyl)acetanilide
(12) 2′-Chloro-5′-[3-(2,4-di-tert-amylphenoxy)propylsulfamoyl]-(2-iso-propylthio-2-methylpropionyl)acetanilide
(13) 2′-Methoxy-5′-[2-(2,4-di-tert-amylphenoxy)-butyramido]-(2-ethylthio-2-methylpropionyl)acetanilide
(14) 2′,4′-Dichloro-{2-[3-(2,4-di-tert-amylphenoxy)-propylthio]-2-methylpropionyl}acetanilide
(15) 2′-Methoxy-5′-[4-(3-n-pentadecylphenoxy)-butyramido]-(2-ethylthio-2-methylpropionyl)acetanilide
(16) 2′-Chloro-5′-[4-(2,4-di-tert-amylphenoxy)-butyramido]-(2-phenylthio-2-methylpropionyl)acetanilide
(17) 2′-Chloro-5′-[2-(2,4-di-tert-amylphenoxy)-butyramido]-(2-phenylthio-2-methylpropionyl)acetanilide
(18) 2′-Methoxy-[2-(3-tolylthio)-2-methylpropionyl]-acetanilide
(19) α-(5,5-Dimethyl-3-hydantoinyl)-α-(2-ethylthio-2-methylpropionyl)-2′-chloro-5′-[4-(2,4-di-tert-amylphenoxy)-butyramido]acetanilide
(20) α-(5,5-Dimethyl-2,4-dioxo-3-oxazolidinyl)-α-(2-ethylthio-2-methylpropionyl)-2′-chloro-5′-[4-(2,4-di-tert-amylphenoxy)butyramido]-acetanilide
(21) α-[5-(or 6-)Bromobenzotriazol-1-yl]-α-(2-ethylthio-2-methylpropionyl)-2′-n-octadecyloxyacetanilide
(22) α-(5,5-Dimethyl-2,4-dioxo-3-oxazolidinyl)-α-(2-ethylthio-2-methylpropionyl)-2′-methoxy-5′-[4-(2,4-di-tert-amylphenoxy)butyramido]acetanilide
(23) α-(4-Carboxyphenoxy)-α-(2-n-octylthio-2-methylpropionyl)-2′-methoxyacetanilide
(24) α-(2,4-Dioxo-1,3-benzoxazin-3-yl)-α-(2-ethylthio-2-methylpropionyl)-2′-chloro-5′-[4-(2,4-di-tert-amylphenoxy)-butyramido]acetanilide
(25) α-(1-Phenyl-5-tetrazolylthio)-α-(2-ethylthio-2-methylpropionyl)-2′-chloro-5′-[4-(2,4-di-tert-amylphenoxy)-butyramido]acetanilide
(26) α-(5-Methyl-2-benzotriazolyl)-α-(2-ethylthio-2-methylpropionyl)-2′-chloro-5′-[4-(2,4-di-tert-amylphenoxy)-butyramido]acetanilide
(27) α-(2,4-Dioxo-1,3-benzoxazin-3-yl)-α-(2-ethylthio-2-methylpropionyl)-2′-methoxy-5′-[4-(2,4-di-tert-amylphenoxy)-butyramido]acetanilide
(28) α-(3-n-Octadecylcarbamoylphenoxy)-α-(2-ethylthio-2-methylpropionyl)-3′,5′-dicarboxyacetanilide
(29) α-(3-n-Octadecylcarbamoylphenylthio)-α-(2-ethylthio-2-methylpropionyl)-3′,5′-dicarboxyacetanilide
(30) N-(2-Benzothiazolyl)-2-ethylthio-2-methylpropionylacetamide
(31) α-(1-Methyl-5-methoxy-3-hydantoinyl)-α-(2-ethylthio-2-methylpropionyl)-2′-methoxy-5′-[4-(2,4-di-tert-amylphenoxy)-butyramido]acetanilide
(32) α-(1-Benzyl-5-methoxy-3-hydantoinyl)-α-(2-ethylthio-2-methylpropionyl)-2′-methoxy-5′-[4-(2,4-di-tert-amylphenoxy)-butyramido]acetanilide Of the yellow color forming couplers represented by the general formula (I) of the present invention, the couplers in which Y is a hydrogen atom can be easily prepared in a overall yield of about 50 to 70% according to a synthesis route shown schematically below.

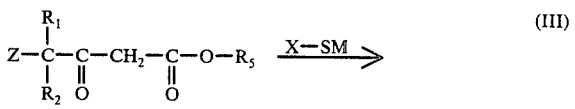

(III)

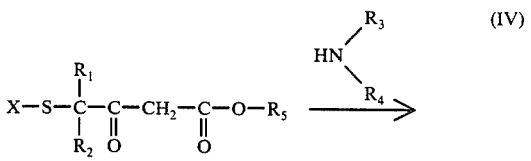

(IV)

-continued $$X-S-\underset{\underset{R_2}{|}}{\overset{\overset{R_1}{|}}{C}}-\underset{\underset{O}{||}}{C}-CH_2-\underset{\underset{O}{||}}{C}-N\overset{R_3}{\underset{R_4}{\diagdown}}\quad(V)$$

in which Z represents a halogen atom such as chlorine or bromine; $R_5$ represents an alkyl group having 1 to 5 carbon atoms such as methyl, ethyl, butyl, etc., or an aryl group such as phenyl, etc.; M represents an alkali metal such as sodium, potassium, etc.; and $R_1$, $R_2$, $R_3$, $R_4$ and X each has the same meaning as defined in general formula (I).

The compound represented by the general formula (III) which is used as a starting material can be easily prepared by a method described in U.S. patent application Ser. No. 369,650 filed June 13, 1973.

The compound represented by the general formula (IV) can be prepared with ease and in high yield by reacting the compound of the general formula (III) with the compound of the formula X-SM in an appropriate organic solvent such as benzene, ethers, e.g., diethyl ether, halogenated hydrocarbons, dimethylformamide, formamide, etc. at about 0° to 40° C.

The compound represented by the general formula (V) can be easily prepared by carrying out a condensation of the compound of the general formula (IV) and the compound of the formula $$HN\overset{R_3}{\underset{R_4}{\diagdown}}$$

using a known method, for example, the method described in U.S. Pat. No. 3,265,506, etc.

Of the yellow color forming couplers represented by the general formula (I) of the present invention, the couplers in which Y is a halogen atom can be easily prepared by a conventional method in which the compound of the general formula (V) is reacted with a molecular halogen in a solvent such as chloroform, carbon tetrachloride, acetic acid, etc.

Further, of the yellow color forming couplers represented by the general formula (I) of the present invention, the couplers in which Y is a group other than a hydrogen atom and a halogen atom can be easily prepared by a method comprising reacting a coupler of the general formula (I) in which Y is a halogen atom with an alkali metal salt of a corresponding coupling off group as described, for example, in U.S. patent application Ser. No. 235,937 filed Mar. 20, 1972, U.S. patent application Ser. No. 319,806 filed Dec. 29, 1972 and U.S. patent application Ser. No. 395,873 filed Sep. 10, 1973, Japanese patent application No. 33238/1973, etc.

Specific synthesis examples are illustrated below. Unless otherwise indicated, all parts, percents, ratios and the like are by weight.

Synthesis Example 1

Preparation of 2'-chloro-5'-[2-(2,4-Di-tert-amylphenoxy)-butyramido]-(2-ethylthio-2-methylpropionyl)acetanilide (Coupler 1)

Step 1: Preparation of Ethyl (2-Ethylthio-2-methylpropionyl)-acetate

To a solution of 31 g of ethylmercaptan and 300 ml of anhydrous benzene, under cooling with an ice bath, 12 g of sodium hydride was added. Thus the sodium salt of ethylmercaptan was formed with the evolution of hydrogen gas. To the mixture, under stirring and cooling with an ice bath, a solution containing 119 g of ethyl (2-bromo-2-methyl-propionyl)acetate obtained by the method described in U.S. patent application Ser. No. 369,650 (filed June 13, 1973) dissolved in 200 ml of anhydrous benzene was added dropwise. After completion of the addition, the reaction mixture was stirred for two hours at room temperature (i.e., 20°–30° C). After the 2 hour period, the reaction mixture was poured into about one liter of ice water, and the mixture was extracted twice, each time with 300 ml of diethyl ether. The extract was washed with water and dried. After removing the solvent, the residue was distilled under reduced pressure to obtain 75 g (yield 68%) of the intended compound which boiled at 80° to 85° C/0.5 mmHg.

Step 2: Preparation of 2'-Chloro-5'-[2-(2,4-di-tert-amylphenoxy)-butyramido]-(2-ethylthio-2-methylpropionyl)acetanilide A mixture of 21.8 g of ethyl (2-ethylthio-2-methylpropionyl)acetate obtained in Step 1 above and 44.5 g of 2-chloro-5-[2-(2,4-di-tert-amylphenoxy)-butyramido]aniline was stirred in an oil bath at 150° C for 3 hours under a reduced pressure of 50 to 100 mmHg. The reaction mixture was recrystallized from ligroin to yield 51 g (yield 83%) of Coupler (1) having a melting point of 65° to 68° C.

Elemental Analysis Calculated (for $C_{34}H_{49}N_2O_4SCl$); C:66.50; H:8.10; N:4.53. Found; C:66.23; H:7.95; N:4.55.

Synthesis Example 2

Preparation of 2'-Chloro-5'-[4-(2,4-di-tert-amylphenoxy)-butyramido]-(2-ethylthio-2-methylpropionyl)acetanilide(Coupler 2)

A mixture of 21.8 g of ethyl (2-ethylthio-2-methylpropionyl)-acetate obtained in Step 1 of Synthesis Example 1, 44.5 g of 2-chloro-5-[4-(2,4-di-tert-amylphenoxy)butyramido]aniline and 500 ml of xylene was refluxed for ten hours. Xylene was distilled off from the reaction mixture, and the residue was recrystallized from acetonitrile to obtain 53 g (yield 87%) of Coupler (2) having a melting point of 121° to 122° C.

Elemental Analysis Calculated (for $C_{34}H_{49}N_2O_4SCl$); C:66.46; H:8.09; N:4.63. Found; C:66.23; H:7.95; N:4.55.

Synthesis Example 3

Preparation of 2'-Methoxy-5'-nitro-(2-ethylthio-2-methylpropionyl)acetanilide (Coupler 7)

A mixture of 21.8 g of ethyl (2-ethylthio-2-methylpropionyl)acetate obtained in Step 1 of Synthesis Example 1 and 16.8 g of 2-methoxy-5-nitroaniline was stirred in an oil bath at 150° C for four hours under a reduced pressure of 50 to 100 mmHg. The reaction mixture was recrystallized from acetonitrile to obtain 29 g (yield 85%) of Coupler (7) having a melting point of 138° to 140° C.

Elemental Analysis Calculated (for $C_{15}H_{20}N_2O_5S$); C:52.89; H:5.94; N:8.36. Found; C:52.88; H:5.88; N:8.23.

Synthesis Example 4

Preparation of
2'-Methoxy-5'-[4-(2,4-di-tert-amylphenoxy)-butyramido]-(2-ethylthio-2-methylpropionyl)acetanilide (Coupler 11)

Step 1: Preparation of
2'-Methoxy-5'-amino-(2-ethylthio-2-methylpropionyl)acetanilide A mixture of 20 g of 2'-methoxy-5'-nitro-(2-ethylthio-2-methylpropionyl)acetanilide obtained in Synthesis Example 3, 20 g of reduced iron, 150 ml of glacial acetic acid, 20 ml of methanol and 20 ml of water was refluxed for 15 minutes under stirring. The reaction mixture was poured into ice water and extracted with ethyl acetate. The extract was washed with water and dried. The solvent was distilled off under reduced pressure. The residue was the substantially pure intended compound.

Step 2: Preparation of
2'-methoxy-5'-[4-(2,4-di-tert-amylphenoxy)-butyramido]-(2-ethylthio-2-methylpropionyl)acetanilide A mixture of 18 g of the residue obtained in Step 1 above 20 g of 4-(2,4-di-tert-amylphenoxy)butyryl chloride, 5 ml of triethylamine and 300 ml of acetonitrile was refluxed for 40 minutes under stirring. The reaction mixture was cooled and the triethylamine hydrochloride deposited was removed by filtration. Acetonitrile was distilled off under reduced pressure from the filtrate. The residue was recrystallized from ethanol to obtain 25 g (yield 70%) of Coupler (11) having a melting point of 57° to 60° C.

Elemental Analysis Calculated (for $C_{35}H_{52}N_2O_5S$); C:68.57; H:8.71; N:4.59. Found; C:68.68; H:8.50; N:4.58.

Synthesis Example 5

Preparation of
2'-Methoxy-5'-[2-(2,4-di-tert-amylphenoxy)-butyramido]-(2-ethylthio-2-methylpropionyl)acetanilide (Coupler 13)

A mixture of 82 g of 2'-methoxy-5'-nitro-(2-ethylthio-2methylpropionyl)acetanilide obtained in Synthesis Example 3 and 800 ml of glacial acetic acid was heated to 90° C. To the mixture, 80 g of reduced iron was gradually added over a four minute period under a nitrogen atmosphere and with stirring. The reaction mixture was cooled to room temperature, and 24.1 g of sodium acetate and then 97 g of 2-(2,4-di-tert-amylphenoxy)butyryl chloride were added, and the mixture was stirred vigorously for 1 hour. The reaction mixture was filtered to remove the insoluble substances. The filtrate was poured into 1 liter of ethyl acetate, washed 4 times, each with 1 liter of a saturated aqueous sodium chloride solution, and then dried with sodium sulfate. After distilling off ethyl acetate, the residue was recrystallized from ethanol to obtain 110 g (yield 75%) of Coupler (13) having a melting point of 65° to 67° C.

Elemental Analysis Calculated (for $C_{35}H_{52}N_2O_5S$); C:68.63; H:8.69; N:4.62. Found; C:68.68; H:8.50; N:4.58.

Synthesis Example 6

Preparation of
2'-n-Octadecyloxy-(2-ethylthio-2-methylpropionyl)acetanilide (Coupler 10)

A mixture of 21.8 g of ethyl (2-ethylthio-2-methylpropionyl)acetate obtained in Step 1 of Synthesis Example 1 and 36.1 g of 2-octadecyloxyaniline was stirred in an oil bath at 150° C for 4 hours under a reduced pressure of 50 to 100 mmHg. The reaction mixture was recrystallized from ethanol to obtain 45.3 g (yield 85%) of Coupler (10) having a melting point of 60° to 62° C.

Elemental Analysis Calculated (for $C_{32}H_{55}NO_3S$); C:70.55; H:10.40; N:2.59. Found; C:70.20; H:10.31; N:2.62.

Synthesis Example 7

Preparation of
2'-Methoxy-(2-n-octadecylthio-2-methylpropionyl)acetanilide (Coupler 4)

Step 1: Preparation of Ethyl
(2-n-Octadecylthio-2-methylpropionyl)acetate

A mixture of 14.3 g of stearylmercaptan and 200 ml of anhydrous benzene was heated with stirring, to which 1.2 g of sodium hydride was gradually added. To the reaction slurry in an ice bath, a solution containing 13.2 g of ethyl (2-bromo-2-methylpropionyl)acetate and 20 ml of anhydrous benzene was gradually added with stirring. After the completion of the addition, the reaction mixture was removed from the ice bath and stirred for three hours. The reaction mixture was then poured into ice water and neutralized by addition of glacial acetic acid. The mixture was extracted with 300 ml of ethyl acetate, the extract was washed twice with a saturated aqueous sodium chloride solution. The ethyl acetate phase was dried with anhydrous sodium carbonate. After distilling off the ethyl acetate, the residue was purified using silica gel chromatography (eluting solvent: chloroform) to obtain 16.2 g (yield 62%) of the intended compound having a melting point of 34° to 37° C.

Step 2: Preparation of
2'-Methoxy-(2-n-octadecylthio-2-methylpropionyl)acetanilide A mixture of 8.0 g of ethyl (2-n-octadecylthio-2-methylpropionyl)acetate obtained in Step 1 above and 3.2 g of o-anisidine was stirred in an oil bath at 140° C for 3 hours under a reduced pressure of 60 mmHg, and then the excess o-anisidine was removed under a reduced pressure of 1mmHg. The reaction mixture was recrystallized from ethanol to obtain 7.9 g (yield 83%) of Coupler (4) having a melting point of 59° to 61° C.

Elemental Analysis Calculated (for $C_{31}H_{53}NO_3S$); C:71.83; H:10.27; N:2.76. Found; C:71.63; H:10.28; N:2.70.

Synthesis Example 8

Preparation of
2'-Chloro-5'-[4-(2,4-di-tert-amylphenoxy)butyramido]-(2-phenylthio-2-methylpropionyl)acetanilide (Coupler 16)

Step 1: Preparation of Ethyl
(2-Phenylthio-2-methylpropionyl)acetate

To a solution of 11.5 g of metallic sodium dissolved in 250 ml of ethanol, 55 g of thiophenol was added, and then ethanol was distilled off. After adding 400 ml of formamide to the residue to form a uniform solution, the solution was immersed in an ice bath, and to the solution 119 g of ethyl (2-ethylthio2-methylpropionyl)acetate was gradually added. After the completion of the addition, the reaction mixture was removed from the ice bath and stirred for three hours. The reaction mixture was poured into one liter of water and extracted twice, each time with 800 ml of diethyl ether. The extract was washed with a saturated aqueous sodium chloride solution and dried with anhydrous sodium carbonate. After distilling off the diethyl ether, the residue was recrystallized from n-hexane to obtain 112 g (yield 84%) of the intended compound having a melting point of 44° to 45° C.

Step 2

Preparation of
2'-Chloro-5'-[4-(2,4-di-tert-amylphenoxy)butyramido]-(2-phenylthio-2-methylpropionyl)acetanilide A mixture of 5.2 g of ethyl (2-Phenylthio-2-methylpropionyl)acetate and 8.8 g of 2-chloro-5-[4-(2,4-di-tert-amylphenoxy)butyramido]aniline in 30 ml of xylene was refluxed for five hours. From the reaction mixture xylene was distilled off, and the residue was recrystallized from acetonitrile to obtain 11.5 g (yield 85%) of Coupler (16) having a melting point of 144° to 145° C.

Elemental Analysis Calculated for $C_{38}H_{47}N_2O_4SCl$); C:68.55; H:7.52; N:4.11. Found; C:68.62; H:7.37; N:4.21.

Synthesis Example 9

Preparation of
2'-Chloro-5'-(2-(2,4-di-tert-amylphenoxy)butyramido]-(2-phenylthio-2-methylpropionyl)acetanilide (Coupler 17)

A mixture of 5.2 g of ethyl (2-phenylthio-2-methylpropionyl)acetate obtained in Step 1 of Synthesis Example 8 and 8.8 g of 2-chloro-5-[2-(2,4-di-tert-amylphenoxy)butyramido]aniline was stirred in an oil bath at 150° C for three hours under a reduced pressure of 15 to 20 mmHg. The reaction mixture was recrystallized from n-hexane to obtain 9.8 g (yield 75%) of Coupler (17) having a melting point of 73° to 75° C.

Elemental Analysis Calculated (for $C_{38}H_{47}N_2O_4SCl$); C:68.36; H:7.47; N:4.21. Found; C:68.62; H:7.37; N:4.21.

Synthesis Example 10

Preparation of
α-(5,5-Dimethyl-2,4-dioxo-3-oxazolidinyl)-α-(2-ethylthio-2-methylpropionyl)-2'-methoxy-5'-[4-(2,4-di-tert-amylphenoxy)butyramido]acetanilide (Coupler 22)

To a solution of 9 g of 2'-methoxy-5'-[4-(2,4-di-tert-amylphenoxy)butyramido]-(2-ethylthio-2-methylpropionyl)acetanilide obtained in Synthesis Example 4 dissolved in 150 ml of carbon tetrachloride, 2.25 g of bromine was gradually added dropwise at room temperature with stirring. After the completion of the addition, the mixture was stirred for 2 hours. The reaction mixture was sufficiently washed with a saturated aqueous sodium chloride solution to obtain a carbon tetrachloride solution of α-bromo-α-(2-ethylthio-2-methylpropionyl)-2'-methoxy-5'-[4-(2,4-di-tert-amylphenoxy)-butyramido]acetanilide. The solution was gradually added dropwise to a solution of 3.5 g of 5,5-dimethyl-2,4-dioxooazolidine, 1.6 g of potassium hydroxide, 20 ml of methanol and 300 ml of dimethylformamide at room temperature under stirring. After the completion of the addition, the reaction mixture was stirred for two hours. The reaction mixture was poured into 500 ml of ethyl acetate, washed sufficiently with a saturated aqueous sodium chloride solution and dried with anhydrous sodium sulfate. After distilling off the solvent, the residue was recrystallized from ethanol to obtain 7.5 g (yield 67%) of Coupler (22) having a melting point of 155° to 156° C.

Elemental Analysis Calculated (for $C_{40}H_{57}N_3O_8S$); C:64.70; H:7.82; N:5.49. Found; C:64.95; H:7.71; N:5.69.

Synthesis Example 11

Preparation of
α-(5,5-Dimethyl-2,4-dioxo-3-oxazolydinyl)-α-(2-ethylthio-2-methylpropionyl)-2'-chloro-5'-[4-(2,4-di-tert-amylphenoxy)butyramido]acetanilide (Coupler 20)

The same procedures as described in Synthesis Example 10 were carried out except for the use of 2'-chloro-5'-[4-(2,4-di-tert-amylphenoxy)butyramido]-(2-ethylthio-2-methylpropionyl)acetanilide obtained in Synthesis Example 2 and 5,5-dimethyl-2,4-dioxooxazolidine to obtain Coupler (20) having a melting point of 145° to 150° C in a yield of 83%.

Elemental Analysis Calculated (for $C_{39}H_{54}N_3O_7SCl$); C:62.88; H:7.35; N:5.57. Found; C:63.00; H:7.32; N:5.65.

Synthesis Example 12

Preparation of α-[5-(or 6-)bromobenzotriazol-1-yl]-α-(2-ethylthio-2-methylpropionyl)-2'-n-octadecyloxyacetanilide (Coupler 21)

The same procedures as described in Synthesis Example 10 were carried out except for the use of 2'-n-octadecyloxy-(2-ethylthio-2-methylpropionyl)acetanilide obtained in Synthesis Example 6 and 5-bromobenzotriazole to obtain Coupler (21) having a melting point of 64° to 66° C in a yield of 69%.

Elemental Analysis Calculated (for $C_{38}H_{57}B_rN_4O_3S$); C:62.54; H:7.88; N:7.83. Found; C:62.53; H:7.87; N:7.68.

Synthesis Example 13

Preparation of
α-(2,4-Dioxo-1,3-benzoxazin-3-yl)-α-(2-ethylthio-2-methylpropionyl)-2'-chloro-5'-[4-(2,4-di-tert-amylphenoxy)butyramido]acetanilide (Coupler 24)

The same procedures as described in Synthesis Example 10 were carried out except for the use of 2'-chloro-5'-[4-(2,4-di-tert-amylphenoxy)butyramido]-(2-ethylthio-2-methylpropionyl)acetanilide obtained in Synthesis Example 2 and 1,3-benzoxazin-2,4-dione to obtain Coupler (24) having a melting point of 194° to 196° C in a yield of 73%.

Elemental Analysis Calculated (for $C_{42}H_{52}N_3O_7ClS$); C:64.70; H:6.73; N:5.60. Found; C:64.78; H:6.68; N:5.41.

Synthesis Example 14

Preparation of
α-(2,4-Dioxo-1,3-benzoxazin-3-yl)-α-(2-ethylthio-2-methylpropionyl)-2'-methoxy-5'-[4-(2,4-di-tert-amylphenoxy)butyramido]acetanilide (Coupler 27)

The same procedures as described in Synthesis Example 10 were carried out except for the use of 2'-methoxy-5'-[4-(2,4-di-tert-amylphenoxy)buryramido]-(2-ethylthio-2-methylpropionyl)acetanilide obtained in Synthesis Example 4 and 1,3-benzoxazin-2,4-dione to obtain Coupler (27) having a melting point of 118° to 120° C in a yield of 76%.

Elemental Analysis Calculated (for $C_{43}H_{55}N_3O_8S$); C:66.74; H:7.29; N:5.36. Found; C:66.67; H:7.11; N:5.43.

The yellow color forming coupler of the present invention represented by the general formula (I) can be used individually or in a combination of two or more. Also the yellow color forming coupler of the present invention can be used together with one or more couplers other than the couplers represented by the general formula (I). Examples of such couplers which can be used include four-equivalent or two-equivalent diketomethylene type yellow color forming couplers such as those described, for example, in U.S. Pat. Nos. 3,277,155; 3,415,652; 3,447,928; 3,408,194; 2,875,057; 3,265,506; 3,409,439; 3,551,155; 3,551,156 and 3,582,322; Japanese patent applications OPI Nos. 26133/1972; 66834/1973; 66835/1973 and 66836/1973; four-equivalent or two-equivalent pyrazolone or imidazolone type magenta color forming couplers such as those described, for example, in U.S. Pat. Nos. 2,600,788; 2,983,608; 3,006,752; 3,062,653; 3,214,437; 3,253,924; 3,311,476; 3,419,391; 3,419,808; 3,476,560 and 3,582,322; Japanese patent publication No. 20636/1970; Japanese patent application OPI No. 26133/1972; four-equivalent or two-equivalent α-naphthol or phenol type cyan color forming couplers such as those described, for example, in U.S. Pat. Nos. 2,474,293; 2,698,794; 3,034,892; 3,214,437; 3,253,924; 3,311,476; 3,458,315; 3,582,322 and 3,591,383; Japanese patent publication Nos. 11340/1967 and 32461/1969. In addition, DIR couplers such as those described, for example, in U.S. Pat. Nos. 3,227,554; 3,297,445; 3,253,924; 3,311,476; 3,379,529; 3,516,831; 3,617,291 and 3,705,801; German patent application OLS No. 2,163,811, can also be used.

The couplers can be incorporated into a photographic material using the methods as described in U.S. Pat. Nos. 2,322,027 and 2,801,171, and the like.

The couplers of the present invention and other couplers can be incorporated into the same or different silver halide emulsion layers or adjacent layers thereof or other layers.

The amount of the coupler employed in the present invention can be varied depending on the type of photographic light-sensitive material and the processing employed. In the case of a coupler-in-the-emulsion type, a range of from about 0.02 to about 1 mole per mole of silver halide in the emulsion layer is particularly preferred. If the amount incorporated is excessively less than about 0.02 mole per mole of silver halide, a large amount of silver halide is required to provide the desired color density, and thus the light-scattering in the emulsion layer tends to increase, which results in a reduction in the sharpness of the images formed. The increase in the coating amount of silver also leads to increase the thickness of the emulsion layer resulting in an increase in the time required for processing. On the other hand, if the amount incorporated is excessively greater than about 1 mole per mole of silver halide, couplers which are not converted to dyes by color development remain in the emulsion layer and reduce the efficiency of coupler utilization. This is disadvantageous from an economical standpoint and results in an increase in the thickness of the emulsion layer accompanied by the above-described disadvantages. When the coupler of the present invention is used out of the above-described range of the amount incorporated, the advantages which can be achieved by the present invention may not be obtained sufficiently.

In the case of a coupler-in-the-developer type, a range from about 0.2 to about 50 g of the coupler per 1000 ml of color developer solution is useful. If the amount added is excessively less than about 0.2 g of the coupler per 1000 ml of the color developer solution, the above-described disadvantages are encountered. On the other hand, if the amount added is excessively greater than about 50 g of the coupler per 1000 ml of the color developer solution, disadvantages in that a large amount of a water-miscible organic solvent must be employed in order to dissolve the coupler in a color developer solution and in that a large amount of alkali is necessary when preparing the color developer solution, in addition to the above-described disadvantages. A particularly preferred amount added ranges from 1 to 10 g per 1000 ml of color developer solution.

The silver halide photographic emulsion which can be used in the present invention comprises a light-sensitive silver halide such as silver chloride, silver bromide, silver chlorobromide, silver chloroiodide, silver iodobromide, silver chloroiodobromide, etc., dispersed in a hydrophilic high molecular weight material, and it can be prepared by various methods.

Suitable hydrophilic high molecular weight materials present in the photographic emulsion include proteins such as gelatin, etc., high molecular weight nonelectrolytes such as polyvinyl alcohol, polyvinyl pyrrolidone, polyacrylamide, etc., high molecular weight amphoteric materials such as a polyacrylamide treated with the Hoffman reaction, a copolymer of acrylic acid N-vinylimidazole, etc.

The silver halide photographic emulsion can also contain various additives which are added to conventional color photographic silver halide emulsions, such as a chemical sensitizing agent, a stabilizer, an antifogging agent, a hardening agent, a spectral sensitizing dye, a surface active agent, and the like.

Examples of suitable chemical sensitizing agents include, for example, gold compounds such as chloroaurates and gold trichloride as described in U.S. Pat. Nos. 2,399,083; 2,540,085; 2,597,856 and 2,597,915; salts of a noble metal, such as platinum, palladium, iridium, rhodium and ruthenium, as described in U.S. Pat. Nos. 2,448,060; 2,540,086; 2,566,254; 2,566,263 and 2,598,079; sulfur compounds capable of forming silver sulfide by reacting with a silver salt, such as those described in U.S. Pat. Nos. 1,574,944; 2,410,689; 3,189,458 and 3,501,313; stannous salts, amines and other reducing compounds such as those described in U.S. Pat. Nos. 2,487,850; 2,518,698; 2,521,925; 2,521,926; 2,694,637; 2,983,610 and 3,201,254, and the like.

Examples of suitable stabilizers or antifogging agents include a wide variety of known compounds such as, for example, heterocyclic compounds, mercury-containing compounds, mercapto compounds or metal salts, including 4-hydroxy-6-methyl-1,3,3a,7-tetraazaindene, 3-methylbenzothiazole and 1-phenyl-5-mercaptotetrazole. Other examples of such commpounds are described, for example, in U.S. Pat. Nos. 1,758,576; 2,110,178; 2,131,038; 2,173,628; 2,697,040; 2,304,962; 2,324,123; 2,394,198; 2,444,605-8; 2,566,245; 2,694,716; 2,697,099; 2,708,162; 2,728,663-5; 2,476,536; 2,824,001; 2,843,491; 2,886,437; 3,052,544; 3,137,577; 3,220,839; 3,226,231; 3,236,652; 3,251,691; 3,252,799; 3,287,135; 3,326,681; 3,420,668 and 3,622,339; and Britis Pat. Nos. 893,428; 403,789; 1,173,609 and 1,200,188; as well as in C. E. K. Mees & T. H. James, *The Theory of the Photographic Process,* Third Ed., MacMillan, New York (1966) and the literature references cited therein.

Examples of suitable hardeners include, for example, an aldehyde type compound such as formaldehyde and glutaraldehyde; a ketone compound such as diacetyl and cyclopentadione; a reactive halogen-containing compound such as bis(2-chloro-ethylurea), 2-hydroxy-4,6-dichloro-1,3,5-triazine and those described in U.S.

Pat. Nos. 3,288,775 and 2,732,303; and British Pat. Nos. 974,723 and 1,167,207; a reactive olefin-containing compound such as divinyl sulfone, 5-acetyl-1,3-diacryloyl-hexahydro-1,3,5-triazine and those described in U.S. Pat. Nos. 3,635,718 and 3,232,763; and British Pat. No. 994,869; an N-methylol compound such as N-hydroxymethylphthalimide and those described in U.S. Pat. Nos. 2,732,316 and 2,586,168; an isocyanate compound such as those described in U.S. Pat. No. 3,103,437; an aziridine compound such as those described in U.S. Pat. Nos. 3,017,280 and 2,983,611; an acid derivative such as those described in U.S. Pat. Nos. 2,725,294 and 2,725,295; a carbodiimide compound such as those described in U.S. Pat. No. 3,100,704; an epoxy compound such as those described in U.S. Pat. No. 3,091,537; an isooxazole type compound such as those described in U.S. Pat. Nos. 3,321,313 and 3,543,292; a halocarboxyaldehyde such as mucochloric acid; a dioxane derivative such as dihydroxydioxane and dichlorodioxane; and an inorganic hardener such as chrome alum and zirconium sulfate. Instead of the above compounds, precursors of hardeners such as the alkali metal bisulfite-aldehyde adducts, methylol derivatives of hydantoin, primary fatty nitroalcohols and the like can also be used.

Suitable spectral sensitizing dyes which can be used include a cyanine dye such as a cyanine, a merocyanine and a carbocyanine. These cyanine dyes can be used individually or in combination. Further, spectral sensitization techniques using a combination of a cyanine dye and a styryl dye can also be employed. Examples of suitable spectral sensitizing dyes are described, for example, in U.S. Pat. Nos. 2,493,748; 2,519,001; 2,977,229; 3,480,434; 3,672,897; 3,703,377; 2,688,545; 3,912,329; 3,397,060; 3,615,635 and 3,628,964; British Pat. Nos. 1,195,302; 1,242,588 and 1,293,862; German patent application OLS Nos. 2,030,326 and 2,121,780; Japanese patent publication Nos. 4936/1968; 14030/1969 and 10773/1968; U.S. Pat. Nos. 3,511,664; 3,522,052; 3,527,641; 3,615,613; 3,615,632; 3,617,295; 3,635,721 and 3,694,217; and British Pat Nos. 1,137,580 and 1,216,203 and the like. The sensitizers can be chosen as desired depending on the spectral range, sensitivity, etc., based on the purposes and uses of the photographic materials to be sensitized.

The surface active agents can be used individually or as a mixture thereof. These are commonly used as a coating aid. However, in some cases they are used for the purpose of emulsifying, dispersing, sensitizing, improving photographic properties, antistatic characteristics, adhesion preventing, or the like.

The surface active agents can be classified as natural surface active agents such as saponin; nonionic surface active agents such as alkylene oxides, glycerols and glycidols; cationic surface active agents such as higher alkylamines, quaternary ammonium salts, heterocyclic compounds such pyridine and the like, phosphoniums or sulfoniums; anionic surface active agents containing an acid group such as a carboxylic acid group, a sulfonic acid group, a phosphoric acid group, a sulfuric acid ester group, or a phosphoric acid ester group; amphoteric surface active agents such as amino acids, aminosulfonic acids, aminoalcohol sulfuric acid esters or amino alcohol phosphoric acid esters. Some examples of those surface active agents which can be used are described, for example, in U.S. Pat. Nos. 2,271,623; 2,240,472; 2,288,226; 2,739,891; 3,068,101; 3,158,484; 3,201,253; 3,210,191; 3,294,540; 3,415,649; 3,441,413; 3,442,654; 3,475,174; 3,545,974; German patent application OLS No. 1,942,665; and British Pat. Nos. 1,077,317 and 1,198,450 as well as Ryohei Oda et al, *Kaimenkasseizai no Gosei to sono Oyo* (*Synthesis and Application of Surface Active Agents*), Maki Shoten (1964); A. W. Perry, *Surface Active Agents*, Interscience Publication Inc. (1958) and J. P. Sisley, *Encyclopedia of Surface Active Agents*, Vol. II, Chemical Publishing Co. (1964).

The photographic emulsion can be applied to a substantially planar material which does not undergo severe dimensional change during processings, for example, a rigid support such as glass, metal or ceramics, or a flexible support as desired. Representative flexible supports include those generally employed for photographic materials, such as a cellulose nitrate film, a cellulose acetate film, a cellulose acetate butyrate film, a cellulose acetate propionate film, a polystyrene film, a polyethylene terephthalate film, a polycarbonate film, a laminate of these polymers, a thin glass film and a paper. A baryta coated paper, a paper which is coated or laminated with a α-olefin polymer, particularly those obtained from an olefin monomer having from 2 to 10 carbon atoms, such as polyethylene, polypropylene and ethylene-butene copolymers, and a synthetic resin film in which the adhesiveness to other polymers and the printing properties are improved by roughening the surfaces thereof, such as described in Japanese patent publication No. 19068/1972 can also be used to advantage as a support.

These supports can be transparent or opaque, depending on the purposes of the photographic materials. Colored transparent supports which contain a dye or pigment can also be used. Such colored supports have been utilized in X-ray films, and are described in *J. SMPTE*, Vol. 67, page 296 (1958).

Examples of opaque supports include opaque films produced by incorporating into a transparent film a dye or a pigment such as titanium oxide and zinc oxide, or surface-treated synthetic resin films such as those described in Japanese patent publication No. 19068/1972, as well as intrinsically opaque materials such as paper. Highly light-shielding papers and synthetic resin films containing, for example, carbon black or dyes can also be used. When the adhesion between a support and a photographic layer is unsatisfactory, a subbing layer which adheres to both of the support and the photographic layer can be provided on the support. The surfaces of the supports can also be pre-treated with a corona discharge, a UV radiation treatment, a flame treatment and the like in order to further improve the adhesiveness.

The photographic layers can be applied to a support using various conventional coating methods, include, for example, a dip coating charge, an air-knife coating method, a curtain coating method and an extrusion coating method using the hopper described in U.S. Pat. No. 2,681,294. If desired, two or more layers can be coated simultaneously using by the methods as described in U.S. Pat. Nos. 2,761,791; 3,508,947; 2,941,898 and 3,526,528.

The photographic light-sensitive material containing the yellow color forming coupler of the present invention can be subjected to color development using an aromatic primary amine compound such as a p-phenylenediamine derivative. Representative examples of color developing agents include N,N-diethyl-p-phenylenediamine, 2-amino-5-diethylaminotoluene, 2-amino-5-(N-ethyl-N-laurylamino)toluene, 4-[N-ethyl- N-(β-hydroxyethyl)amino]-aniline, and the inorganic acid salts thereof, 4-amino-3-methyl-N-ethyl-N-(β-methanesulfonamidoethyl)aniline sesquisulfate monohydrate as described in U.S. Pat. No. 2,193,015, N-(2-amino-5-diethylaminophenylethyl)methanesulfonamide sulfate as described in U.S. Pat. No. 2,592,364, N,N-dimethyl-p-phenylenediamine hydrochloride, 3-methyl-4-amino-N-ethyl-N-methoxyethylaniline as described in Japanese patent application OPI No. 64933/1973, and the like. Color developing agents are also described in greater detail in L. F. A. Mason *Photographic Processing Chemistry*, pages 226 to 229, Focal Press, London (1966). Also 3-pyrazolidones can be used together with these p-phenylenediamine type developing agents.

The color developer solution can optionally contain various additives. Typical examples of such additives include alkaline agents (for example, alkali metal or ammonium hydroxides, carbonate or phosphates); pH-adjusting agents or buffers (for example, weak acids such as acetic acid, boric acid, etc., weak alkalis, or the salts thereof); developing accelerators (for example, various pyridinium compounds or cationic compounds such as those described in U.S. Pat. Nos. 2,648,604 and 3,671,247; potassium nitrate; sodium nitrate; condensation products of polyethylene glycol, and their derivatives such as those described in U.S. Pat. Nos. 2,533,990; 2,577,127 and 2,950,970; nonionic compounds such as polythioethers represented by those described in British Pat. Nos. 1,020,033 and 1,020,032; polymeric compounds having sulfite ester groups such as those described in U.S. Pat. No. 3,068,097; organic amines such as pyridine and ethanolamine; benzyl alcohol; hydrazines and the like); anti-fogging agents (for example, alkali metal bromides; alkali metal iodides; nitrobenzimidazoles such as those described in U.S. Pat. Nos. 2,496,940 and 2,656,271; mercaptobenzimidazole; 5-methylbenztriazole; 1-phenyl-5-mercaptotetrazole; compounds for use in rapid processing solutions such as those described in U.S. Pat. Nos. 3,113,864; 3,342,596; 3,295,976; 3,615,522 and 3,597,199; thiosulfonyl compounds such as those described in British Pat. No. 972,211; phenazine-N-oxides such as those described in Japanese patent publication No. 41675/1971; those described in *Kagaku Shashin Binran* (*Manual of Scientific Photography*) Vol. II, pages 29–47 and the like); stain or sludge preventing agents such as those described in U.S. Pat. Nos. 3,161,513 and 3,161,514; and British Pat. Nos. 1,030,422; 1,144,481 and 1,251,558; interlayer-effect accelerators desclosed in U.S. Pat. No. 3,536,487; preservatives (for example, sulfites, bisulfites, hydroxyamine hydrochloride, formsulfite, alkanolaminesulfite adducts, etc.) and the like.

The couplers of the present invention can be used by addition to such color developer solutions.

In case of color reversal light-sensitive materials, a black and white development step is used prior to the color development. Suitable developing agents which can be used include 4-aminophenols such as 4-N-methylaminophenol hemisulfate, 4-N-benzylaminophenol hydrochloride, 4-N,N-diethylaminophenol hydrochloride, 4-aminophenol sulfate, etc.; 3-pyrazolidones such as 1-phenyl-3-pyrazolidone, 4,4-dimethyl-1-phenyl-3-pyrazolidone, 4-methyl-1-phenyl-3-pyrazolidone, etc.; polyhydroxybenzenes such as hydroquinone, 2-methylhydroquinone, 2-phenylhydroquinone, 2-chlorohydroquinone, pyrogallol, catechol, etc.; p-phenylenediamines such as p-phenylenediamine hydrochloride, N,N-diethyl-p-phenylenediamine sulfate, etc.; ascorbic acid; N-(p-hydroxyphenyl)glycine; and those described in C. E. K. Mees and T. H. James, *The Theory of the Photographic Process*, 3 Ed., Chapter 13, MacMillan Co. (1966) and L. F. A. Mason, *Photographic Processing Chemistry*, pages 16 to 30, Oxford Press (1966). Mixtures of these developing agents can also be used.

After color development, the color photographic materials are subjected to a bleaching. The bleaching can be simultaneously carried out together with the fixing. A bleaching bath can be converted to a blixing bath by adding a fixing agent, if desired. Many compounds can be used as a bleaching agent. Of these bleaching agents, ferricyanides; bichromates; water-soluble cobalt (III) salts, water-soluble copper (II) salts; water-soluble quinones; nitrosophenol; compounds of a polyvalent metal such as iron (III); cobalt (III), copper (II), etc., especially, complex salts of such a polyvalent cation, and an organic acid, for example, an aminopolycarboxylic acid such as ethylenediaminetetraacetic acid, nitrilotriacetic acid, iminodiacetic acid, N-hydroxyethylethylenediaminetriacetic acid, etc., malonic acid, tartaric acid, malic acid, diglycolic acid and dithioglycolic acid, and 2,6-dipicollinic acid; peracids such as alkylperacids, persulfates, permanganates and peroxides; hypochlorites; chlorine; bromine; and the like can be suitably used, individually or in combination. To the bleaching solution, bleaching accelerators such as those described in U.S. Pat. Nos. 3,042,520 and 3,241,966; and Japanese patent publication Nos. 8506/1970 and 8836/1970 and various other additives can be employed.

The coupler of the present invention has a high coupling reactivity for an oxidation product of an aromatic primary amine developing agent and rapidly removes the oxidation product of the developing agent formed during color development, so that the development of the silver halide emulsion is accelerated.

The coupler of the present invention provides, upon coupling with an oxidation product of an aromatic primary amine developing agent, a dye which has superior spectral absorption properties in that it has a pure yellow color without any redish tint due to less absorption in a longer wavelength region, and thus exhibits an excellent color reproducibility in the subtractive color process.

The dye image formed from the reaction of the coupler of the present invention with an oxidation product of an aromatic amine developing agent is stable and less sensitive to light and humidity, and thus has an extremely less tendency toward fading during storage under severe conditions for a long period of time. Therefore, the color photographic image can be stored for a long period of time.

The coupler of the present invention can be prepared in high yield using raw materials which are industrially readily available. Furthermore, in the compound represented by the general formula (I), it is possible to modify the properties of the coupler depending on the purposes of use of a photographic light-sensitive material by selecting a suitable group for X. While in order to render a pivaloyl acetanilide type coupler diffusion resistant, the introduction of a ballasting group is restricted to the anilide ring, the degree of freedom to introduce a ballasting group into the coupler of the present invention is doubly increased, and thus it is easy to provide the coupler with the required sufficient properties.

The present invention will be further explained in greater detail by reference to the following examples.

EXAMPLE 1

A solution prepared by heating at a temperature of 45° C a mixture of 23.1 g of Coupler (1) of the present invention, 2'-chloro-5'-[2-(2,4-di-tert-amylphenoxy)-butyramido]-(2-ethylthio-2-methylpropionyl)acetanilide, 25 ml of di-n-butyl phthalate and 50 ml of ethyl acetate was added to 250 ml of an aqueous solution containing 25 g of gelatin and 2.5 g of sodium dodecylbenzene sulfonate. The mixture was stirred and then agitated vigorously in a high speed agitator for 30 minutes. The couplers were finely dispersed together with the solvent.

All of the dispersion was added to 1.0 Kg of a photographic emulsion containing 54 g of silver iodobromide (iodine content: 5 mole %) and 65 g of gelatin, and to which 30 ml of a 3% acetone solution of triethylene phosphoramide was added as a hardener. The pH of the mixture was adjusted to 6.0 and then the mixture was applied onto a cellulose triacetate film support in a dry thickness of 7.0 microns. This material was designated Sample A. The sample contained $2.0 \times 10^{-3}$ mole of the coupler per square meter of the support.

A film was prepared using the same procedure as described above except for the use of 25.0 g of Coupler (17) of the present invention, 2'-chloro-5'-[2-(2,4-di-tert-amylphenoxy)butyramido]-(2-phenylthio-2-methylpropionyl)acetanilide in place of Coupler (1). This film was designated Sample B. The sample contained $2.0 \times 10^{-3}$ mole of the coupler per square meter of the support.

For comparison, another film was prepared using the same procedure as described above except that there was used, in place of Coupler (1), 21.5 g Coupler (a), 2'-chloro-5'-[2-(2,4-di-tert-amylphenoxy)butyramido]-pivaloylacetanilide, which is a compound corresponding to the Coupler (1), and Coupler (17). This film was designated Sample C. The sample contained $2.1 \times 10^{-3}$ mole of the coupler per square meter of the support.

These films were subjected to sensitometric stepwise exposure followed by processing in the following manner.

|   | Processing Step | Temperature (° C) | Time (min.) |
|---|---|---|---|
| 1. | Color Development | 20 | 15 |
| 2. | Washing | 18 | 1 |
| 3. | First Fixing | 20 | 4 |
| 4. | Washing | 18 | 3 |
| 5. | Bleaching | 20 | 5 |
| 6. | Washing | 18 | 3 |
| 7. | Second Fixing | 20 | 3 |
| 8. | Washing | 18 | 15 |

The composition of the color developer solution used herein was as follows:

| Color Developer Solution A | |
|---|---|
| Sodium Sulfite (anhydrous) | 3.0 g |
| Sodium Carbonate (monohydrate) | 47.0 g |
| 4-Amino-3-methyl-N,N-diethylaniline Hydrochloride | 2.5 g |
| Potassium Bromide | 2.0 g |
| Water to make | 1,000 ml |

The fixing solution used was an aqueous acidic solution containing sodium thiosulfate and sodium sulfite, and the bleaching solution used was a neutral solution containing potassium ferricyanide and potassium bromide.

After the processing, the transmission optical density to blue light of these samples was measured thereby the following photographic characteristics as shown in Table 1 below were obtained. The resulting color images, in either case, were clear yellow having an absorption maximum at 456 millimicrons.

Table 1

| Film Sample | Coupler | Fog | Sensitivity* | Gamma | Maximum Density |
|---|---|---|---|---|---|
| A | (1) | 0.07 | 100 | 1.33 | 1.70 |
| B | (17) | 0.08 | 101 | 1.45 | 1.85 |
| C | (a) | 0.09 | 99 | 1.26 | 1.64 |

*Relative value of exposure amount required to provide a density of fog + 0.10.

The maximum densities are shown in the following Table 2, which were obtained upon processing each sample for different periods of developing time.

Table 2

| Film Sample | Coupler | Developing Time (min.) | | |
|---|---|---|---|---|
| | | 10 | 15 | 20 |
| A | (1) | 1.56 | 1.70 | 1.75 |
| B | (17) | 1.73 | 1.85 | 1.89 |
| C | (a) | 1.48 | 1.64 | 1.70 |

These results show that the couplers of the present invention can provide higher sensitivity, gradation and color density, in comparison with the known coupler, a pivaloyl acetanilide type coupler. Such results indicate that the couplers of the present invention have a higher coupling activity than pivaloyl acetanilide type couplers.

In order to demonstrate this improved coupling reactivity the following experiment was carried out.

Coupler (1) and Coupler (17) of the present invention and Coupler (a) each was mixed with a cyan color forming coupler (b), i.e., 4,6-dichloro-5-methyl-2-[α-(2,4-di-tert-amylphenoxy)acetamido]phenol in a molar ratio of 2:1 and color development, using 4-amino-3-methyl-N,N-diethylaniline, was carried out. The analysis of the ratio of the formed yellow dye to the cyan dye, from which the relative value, based upon the cyan forming coupler (b), of the reaction rate constant in the coupling reaction of the yellow forming coupler was calculated. The relative value of the reaction rate constant was determined by measuring the amounts of the two couplers in the color image obtained by mixing two couplers X and Y which produce clearly separated different colors and adding the mixture to an emulsion, and then performing color development. If coupler X develops color of the maximum density $(D_X)_{max}$ and color of $D_X$ in an intermediate stage, and coupler Y develops colors of $(D_Y)_{max}$ and $D_Y$ respectively, the ratio $R_X/R_Y$ of the reaction activities of both couplers is expressed by the following equation.

$$\frac{R_X}{R_Y} = \frac{\log(1 - \frac{D_X}{(D_X)_{max}})}{\log(1 - \frac{D_Y}{(D_Y)_{max}})}$$

The coupling reactivity ratio $R_X/R_Y$ can be obtained from the slope of the straight line which is obtained by plotting several sets of $D_X$ and $D_Y$ results from using several stages of exposure of an emulsion containing a mixed coupler and subjecting them to color development, on two axes crossing at right angles to each other as log $(1 - D/D_{max})$. Coupler (1) and Coupler (17) of the present invention had a relative rate constant of 0.41 and 0.56, respectively, while the pivaloyl acetanilide type coupler (a) had a relative rate of 0.32. These results clearly illustrate that the couplers of the present invention have a high coupling reactivity and provide high sensitivity, gradation and color density.

EXAMPLE 2

Each of Sample A, B and C prepared in Example 1 was subjected to sensitometric stepwise exposure and then processed in the same manner as described in Example 1. The samples thus obtained were subjected to storage under exposure to a xenon arc lamp of 1.5 KW (150,000 lux) through a UV-filter which absorbed substantialy all light having wave lengths shorter than 400 millimicrons for 70 hours and the light fastness of the color images was measured. The results obtained are shown in Table 3.

Table 3

| Film Sample | Coupler | Xenon Arc (150,000 lux): 70 Hours | | |
|---|---|---|---|---|
| | | Do=0.5 | 1.0 | 1.5 |
| A | (1) | 37* | 27 | 25 |
| B | (17) | 42 | 35 | 32 |
| C | (a) | 50 | 45 | 41 |

*The rate of fading from the initial density to blue light (Do) in percentage.

Also Samples A, B and C which were subjected to the same processing were stored under conditions of high temperature and high humidity, i.e., at 60° C, 75% RH, for three weeks and the fastness of the color images was measured. The results obtained are shown in Table 4.

Table 4

| Film Sample | Coupler | 60° C, 75% RH: 3 Weeks | | |
|---|---|---|---|---|
| | | Do=0.5 | 1.0 | 1.5 |
| A | (1) | 5* | 4 | 3 |
| B | (17) | 6 | 4 | 4 |
| C | (a) | 7 | 5 | 4 |

*The rate of fading from the initial density to blue light (Do) in percentage.

From these results it is apparent that the couplers of the present invention provide color images of excellent fastness.

EXAMPLE 3

A solution prepared by heating and dissolving at a temperature of 50° C a mixture of 29.6 g of Coupler (22) of the present invention, α-(5,5-dimethyl-2,4-dioxo-3-oxazolidinyl)-α-(2-ethylthio2-methylpropionyl)-2'-methoxy-5'-[4-(2,4-di-tert-amylphenoxy)-butylamino]acetanilide, 30 ml of di-n-butyl phthalate and 50 ml of butyl acetate was added to 300 ml of an aqueous solution containing 3.0 g of sodium di-(2-ethylhexyl)-α-sulfosuccinate and 30 g of gelatin. The mixture was stirred and then passed five times through a preheated colloid mill. The couplers were finely dispersed together with the solvent.

All of the dispersion was mixed with 700 g of a photographic emulsion containing 22.6 g of silver iodobromide (iodide content: 2 mole %) and 50 g of gelatin, to which 20 ml of a 3% acetone solution of triethylene phosphoramide was added as a hardener. The mixture was then adjusted to a pH of 6.5 and applied in a dry thickness of 3.5 microns onto a photographic paper support, both surfaces of which had been resin-coated with polyethylene.

On the resulting coating, was applied a gelatin solution in a dry thickness of 1.0 microns to form a second layer.

A green-sensitive silver halide emulsion containing a magenta color forming Coupler (c) of the structure shown below was then applied in a dry thickness of 3.5 microns to form a third layer.

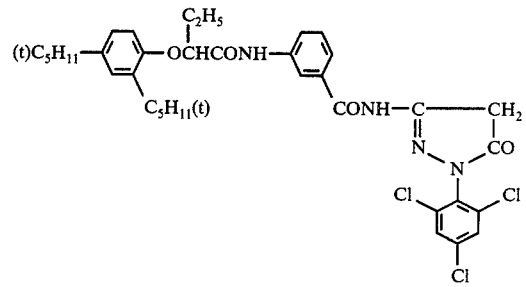

A gelatin solution containing 2-(2'-benzotriazolyl)4,6-dibutylphenol as an ultraviolet absorbing agent was then applied in a dry thickness of 2.5 microns to form a fourth layer. A red-sensitive silver halide emulsion containing a cyan color forming Coupler (d) of the structure shown below was applied in a dry thickness of 4.0 microns to form a fifth layer and finally a gelatin solution was applied in a dry thickness of 0.5 micron to form the uppermost layer, thereby producing a color printing paper.

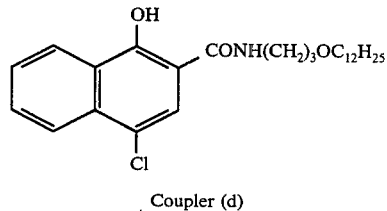

Coupler (d)

This color print paper was optically printed from a color negative and processed in the following manner.

| | Processing Step | Temperature (° C) | Time (min.) |
|---|---|---|---|
| 1. | Color Development | 24 | 8 |
| 2. | Stopping | " | 2 |
| 3. | Blixing | " | 6 |
| 4. | Washing | " | 5 |

The composition of the color developer solution used was as follows

| Color Developer Solution | |
|---|---|
| Benzyl Alcohol | 12.0 ml |
| Sodium Hexametaphosphate | 2.0 g |
| Sodium Sulfite (anhydrous) | 2.0 g |
| Sodium Carbonate (monohydrate) | 27.5 g |
| Hydroxylamine Sulfate | 2.5 g |
| 4-Amino-3-methyl-N-ethyl-N-(3-methanesulfonamidoethyl)-aniline Sesquisulfate (monohydrate) | 4.0 g |
| Water to make | 1000 ml |

The compositions of the other processing solutions were as follows.

| Stopping Solution | |
|---|---|
| Sodium Sulfite (anhydrous) | 5.0 g |
| Glacial Acetic Acid | 15.0 ml |

-continued

Stopping Solution

| | |
|---|---|
| Water to make | 1000 ml |

Blixing Solution

| | |
|---|---|
| Ammonium Thiosulfate | 105.0 g |
| Sodium Sulfate | 8.0 g |
| Sodium Hydroxide | 18.0 g |
| EDTA Disodium Salt | 35.0 g |

The resulting color print had a clear color and had excellent color reproducibility. Particularly, the freedom from any red tint in the yellow color was marked. The yellow dye image had an absorption maximum at 447 millimicrons.

This color print was directly exposed to sun light for ten days, but, the density decrease for the yellow dye image in the area of an initial reflection density of 1.0 was only 0.08. When it was stored at high temperature and humidity conditions, i.e., at 60° C, 75% RH, for ten days, no substantial decrease in the density was observed.

EXAMPLE 4

A solution prepared by heating at 45° C a mixture of 25.0 g of Coupler (16) of the present invention, 2'-chloro-5'-[4-(2,4di-tert-amylphenoxy)butyramido]-(2-phenylthio-2-methylpropionyl)acetanilide, 25 ml of tri-n-hexylphosphate and 40 ml of ethyl acetate was added to 250 ml of an aqueous solution containing 25 g of gelatin and 1.25 g of sodium cetylsulfate. The mixture was stirred and then agitated vigorously in a high speed agitator for 30 minutes. The couplers were finely dispersed together with the solvent.

All of the dispersion was added to 1.0 kg of a photographic emulsion containing 0.30 mole of silver bromide and 75 g of gelatin, and then 10 ml of a 4% aqueous solution of the sodium salt of 2-hydroxy-4,6-dichloro-s-triazine was added as a hardener. After adjusting the pH to 6.5, the mixture was coated on a cellulose triacetate film support in a dry thickness of 7.0 microns. This material was designated Sample D. The sample contained $1.9 \times 10^{-3}$ mole of the coupler per square meter of the support.

For comparison, a film was prepared by carrying out the same procedure as described above except for the use of 25.0 g of Coupler (e), 2'-chloro-5'-[4-(2,4-di-tert-amylphenoxy)butyramido]-(2-phenoxy-2-methylpropionyl)acetanilide, which is a coupler described in German patent application OLS No. 2,162,899 in place of Coupler (16). This film was designated Sample E. This sample contained $1.9 \times 10^{-3}$ mole of the coupler per square meter of the support.

These samples were subjected to sensitometric stepwise exposure and processed in the same manner as described in Example 1 except that the color development step was carried out at 24° C for 12 minutes using Color Developer Solution B described in Example 3.

After the processing, the transmission optical density to blue light of these samples was measured, and the photographic properties obtained are shown in Table 5.

Table 5

| Sample | Coupler | Fog | Sensitivity* | Gamma | Maximum Density |
|---|---|---|---|---|---|
| D | (16) | 0.06 | 100 | 1.24 | 1.65 |
| E | (e) | 0.06 | 99 | 1.19 | 1.61 |

*Relative value of exposure amount required to provide a density of fog + 0.10.

Further, Samples D and E which were subjected to the same processing were stored under a high temperature condition at 100° C for 3 hours and the fastness of the color images was measured. The results obtained are shown in Table 6.

Table 6

| | | 100° C : 3 Hours | | |
|---|---|---|---|---|
| Sample | Coupler | Do=0.5 | 1.0 | 1.5 |
| D | (16) | 2 | 1 | 1 |
| E | (e) | 3 | 3 | 2 |

The above results clearly demonstrate that the coupler of the present invention has superior characteristics in photographic properties and fastness of color images in comparison with a known similar coupler.

EXAMPLE 5

A solution prepared by heating at 60° C a mixture of 24.1 g of Coupler (20) of the present invention α-(5,5-dimethyl-2,4-dioxo-3-oxazolidinyl)-α-(2-ethylthio-2-methylpropionyl)-2'-chloro-5'-[4-(2,4-di-tert-amylphenoxy)butyramido]acetanilide, 25 ml of di-n-butyl phthalate, 1.0 g of 2.5-dioctyl hydroquinone and 35 ml of cyclohexanone was added to 250 ml. of an aqueous solution containing 1.5 g of sodium p-dodecylbenzene sulfonate and 25 g of gelatin. The mixture was stirred and then passed five times through a preheated colloid mill, thereby providing a fine dispersion of the coupler together with the solvent.

All of the coupler dispersion was added to 500 g of a photographic emulsion containing 27.2 g of silver iodobromide (iodide content: 4.5 mole%) and 35 g of gelatin, and then 12.5 ml of a 3% acetone solution of triethylene phosphoramide was added as a hardener. After adjusting the pH to 6.5, a coating solution for a blue-sensitive emulsion layer was prepared.

On a polyethylene terephthalate film support, were coated, as a first layer, a gelatin solution containing black colloidal silver in a dry thickness of 2.5 microns for antihalation; as a second layer, a red-sensitive silver halide emulsion containing a cyan color forming Coupler (b), 4,6-dichloro-5-methyl-2-[α-(2,4-di-tert-amylphenoxy)acetamido]phenol in a dry thickness of 4.5 microns; as a third layer, a gelatin solution containing 2,5-di-tert-octylhydroquinone in a dry thickness of 1.5 microns; as a fourth layer, a green-sensitive silver halide emulsion layer containing a magenta color forming Coupler (d), 1-(2,6-dichloro-4-methoxyphenyl)-3-{3-[α-(2,4-di-tert-amylphenoxy)butyramido]-benzamido}-5-pyrazolone in a dry thickness of 4.5 microns; and as a fifth layer, a gelatin layer containing yellow colloidal silver in a dry thickness of 2.0 microns. On the fifth layer, were coated the above-described coating solution for the blue-sensitive emulsion layer in a dry thickness of 2.0 microns, and as an uppermost layer, a gelatin protective layer in a dry thickness of 1.0 micron, thereby preparing a color photographic film. The film was exposed to light and subjected to the following processing.

| Processing Step | Temperature (° C) | Time (min.) |
|---|---|---|
| First Development (black and white development) | 21 | 3 |
| Washing | 18 | 10 |
| Uniform Exposure | | |
| Second Development (color development) | 21 | 12 |
| Stopping | 21 | 2 |
| Blixing | 21 | 8 |
| Washing | 18 | 10 |

In the second development (color development) Color Developer Solution B described in Example 3 was used, and also in the blixing, the blixing solution described in Example 3 was used. In the first development a black and white developer solution (Developer Solution C) of the following composition was used.

| Developer Solution C | |
|---|---|
| p-N-Methylaminophenol | 0.3 g |
| Sodium Sulfite (anhydrous) | 38.0 g |
| Sodium Carbonate (monohydrate) | 22.5 g |
| Potassium Bromide | 0.9 g |
| Citric Acid | 0.7 g |
| Potassium Thiocyanate | 1.0 g |
| Water to make | 1000 ml | the reversal color photographic image thus obtained had a clear color and exhibited excellent color reproducibility. Also the sharpness of the color images was improved due to a decrease in the thickness of the blue-sensitive emulsion layer.

EXAMPLE 6

A silver iodobromide emulsion (iodide content: 2 mole %) was coated in a dry thickness of 5.0 microns and a silver coating amount of 150 micro grams per square centimeter to prepare a film. The film was subjected to sensitometric stepwise exposure and then developed at 24° C for 10 minutes using the developer solution set forth below and followed fixing, washing, bleaching, washing, fixing, and washing in the manner as described in Example 1 to provide a yellow dye image.

| Color Developer Solution D | |
|---|---|
| Sodium Sulfite (anhydrous) | 1.0 g |
| 4-Amino-3-methyl-N,N-diethylaniline Hydrochloride | 2.0 g |
| Sodium Carbonate (monohydrate) | 22.5 g |
| Potassium Bromide | 1.0 g |
| 4'-Chloro-(2-ethylthio-2-methylpropionyl)-acetanilide (Coupler (6) of the present invention) | 2.0 g |
| Acetone | 20.0 ml |
| Sodium Hydroxide (8% aqueous solution) | 25.0 ml |
| Water | 950 ml |

The color image obtained exhibited a spectral absorption property having an absorption maximum at 455 millimicrons.

EXAMPLE 7

A solution prepared by heating at 60° C a mixture of 48.2 g of Coupler (20) of the present invention, α-(5,5-dimethyl-2,4-dioxo-3-oxazolidinyl)-α-(2-ethylthio-2-methylpropionyl)-2'-chloro-5'-[4-(2,4-di-tert-amylphenoxy)butyramido]acetanilide, 50 ml of di-n-butyl phthalate and 75 ml of cyclohexanone was added to 500 ml of an aqueous solution containing 2.5 g of sodium p-dodecylbenzene sulfonate and 50 g of gelatin. The mixture was stirred and then passed five times through a preheated colloid mill, thereby providing a fine dispersion of the coupler together with the solvent.

All of the coupler dispersion was mixed with 1.0 Kg of a photographic emulsion containing 123 g of silver iodobromide (iodide content: 7.0 mole %) and 60 g of gelatin, and then 20 ml of a 4% aqueous solution of 2-hydroxy-4,6-dichloro-s-triazine sodium salt was added as a hardener. After adjusting the pH to 6.5, the mixture was coated on a cellulose triacetate film support in a dry thickness of 5.0 microns. This film was designated Sample F.

The same procedure as for Sample F was carried out except for the use of 45.8 g of Coupler (20) and 2.7 g of Coupler (25) of the present invention, α-(1-phenyl-5-tetrazolylthio)-α-(2-ethylthio-2-methylpropionyl)-2'-chloro-5'-[4-(2,4-di-tert-amylphenoxy)-butyramido]acetanilide to prepare Sample G.

Samples F and G were subjected to a slim line exposure of a 500 micron slit width with X-rays and then processed at 38° C according to the following processing steps.

| 1. | Color Development | 3 min. and 15 sec. |
|---|---|---|
| 2. | Bleaching | 6 min. and 30 sec. |
| 3. | Washing | 3 min. and 15 sec. |
| 4. | Fixing | 6 min. and 30 sec. |
| 5. | Washing | 3 min. and 15 sec. |
| 6. | Stabilizing | 3 min. and 15 sec. |

The compositions of the processing solutions used in the respective steps were as follows:

| Color Developer Solution | |
|---|---|
| Sodium Nitrilotriacetate | 1.0 g |
| Sodium Sulfite | 4.0 g |
| Sodium Carbonate | 30.0 g |
| Potassium Bromide | 1.4 g |
| Hydroxylamine Sulfate | 2.4 g |
| 4-(N-Ethyl-N-β-hydroxyethylamino)-2-methylaniline Sulfate | 4.5 g |
| Water to make | 1 liter |

| Bleaching Solution | |
|---|---|
| Ammonium Bromide | 160 g |
| Aqueous Ammonia (28%) | 25.0 ml |
| Sodium Ethylenediaminetetraacetate Iron Salt | 130 g |
| Glacial Acetic Acid | 14 ml |
| Water to make | 1 liter |

| Fixing Solution | |
|---|---|
| Sodium Tetrapolyphosphate | 2.0 g |
| Sodium Sulfite | 4.0 g |
| Ammonium Thiosulfate (70%) | 175.0 ml |
| Sodium Bisulfite | 4.6 g |
| Water to make | 1 liter |

| Stabilizing Solution | |
|---|---|
| Formalin (40%) | 8.0 ml |
| Water to make | 1 liter |

After processing in the above described manner, the optical density to blue light of the samples was measured using a microdensitometer and the following results were obtained.

Table 7

| Sample | Area Measured | Optical Density |
|---|---|---|
| E | Center | 1.51 |
| " | Edge | 1.54 |
| F | Center | 1.25 |
| " | Edge | 1.52 |

In Sample E, substantially no density difference between the center area and edge area was observed. On the contrary, in Sample F, a large density difference between the center area and edge area was observed. That is, a large edge effect extent was observed. The edge effects have the function of markedly improving the resolving power and sharpness of a photographic light-sensitive material. By substituting one of the hydrogen atoms on the active methylene group in the coupler of the present invention with another appropriate group, the property described in the present example can be provided to the coupler in addition to the properties in that the coupling reactivity is high, in that a rapid processing is applied and in that dye formation and silver removal are completed in a weak oxidizing bath.

EXAMPLE 8

A solution prepared by heating and dissolving at 70° C a mixture of 59 g of Coupler (28) of the present invention, α-(3-n-octadecylcarbamoylphenoxy)-α-(2-ethylthio-2-methylpropionyl)-3',5'-dicarboxyacetanilide, 90 ml of N,N-diethyldodecylamide and 90 ml of cyclohexanone was added to 600 ml of an aqueous solution containing 3.0 g of sodium p-dodecylbenzene sulfonate and 60 g of gelatin. The mixture was stirred and then passed five times through a preheated colloid mill, thereby providing a fine dispersion of the coupler together with the solvent.

All of the coupler dispersion was mixed with 1 Kg of a photographic emulsion containing 76.0 g of silver iodobromide (iodide content: 5.0 mole%) and 65 g of gelatin, and then 25 ml of a 4% aqueous solution of 2-hydroxy-4,6-dichloro-s-triazine sodium salt was added as a hardener. The mixture was coated on a cellulose acetate support in a dry thickness of 5.0 microns and on the resulting layer a gelatin solution was coated in a dry thickness of 1.0 micron as a protective layer to prepare a light-sensitive element.

On a polyethylene terephthalate base were coated, in order, the following layers to prepare an image receiving sheet.

(1) A neutralizing layer comprising 300 mg/100 cm² of the half ester obtained by treating a (1:1 molar ratio) copolymer of vinyl methyl ether and maleic anhydride with butyl alcohol and 60 mg/100 cm² of 1,4-bis(2',3'-epoxypropoxy)butane.

(2) A neutralization rate-controlling layer comprising 45 mg/100 cm² a copolymer of n-butylacrylate and β-hydroxyethylmethacrylate (monomer ratio : about 1:1).

(3) An image receiving layer comprising 18 mg/100 cm² of cetyl-tri-n-butyl ammonium chloride, 40 mg/100 cm² of gelatin and 2 mg/100 cm² of tetramethylol urea.

(4) A covering layer of a thickness of about 0.5 microns prepared by treating the surface with a 1% acetone solution of polyethyleneglycol monocetyl ether.

A processing solution having the composition set forth below was prepared and incorporated into a rupturable container. The container was prepared by folding a laminate film of polyethylene, alminium, cellophane and polyethylene and heat-sealing so as to form a space for retaining the processing solution. The preparation and the incorporation of the precessing solution into the container were carried out in a Freon gas.

| | |
|---|---|
| Water | 100 ml |
| Ascorbic Acid | 20 mg |
| 4-Amino-3-methyl-N-ethyl-N-(β-hydroxyethyl)aniline Sulfate (monohydrate) | 2.8 g |
| 4-Nitrobenzimidazole Nitrate | 15 mg |
| Sodium Hydroxide | 4 g |
| Sodium Carboxymethyl Cellulose | 3.5 g |
| Titanium dioxide | 45 g |

The light-sensitive material and the image receiving material described above were cut into an appropriate size for testing, the coated surfaces of each material were faced toward each other, and between these materials, at one of the edges, the container retaining the processing solution was tightly positioned.

The film unit thus prepared was subjected to exposure and passed through a pair of pressure rollers to rupture the container and the processing solution was uniformly spread in a spread thickness of 120 microns.

After three minutes, a clear yellow negative image formed on the image receiving layer was observed. Measurement of the reflection density using blue light showed a maximum density of 1.5 and a minimum density of 0.3.

While the invention has been described in detail and with reference to specific embodiments thereof, it will be apparent to one skilled in the art that various changes and modifications can be made therein without departing from the spirit and scope thereof.

What is claimed is:

1. A photographic silver halide emulsion containing a coupler represented by the following formula

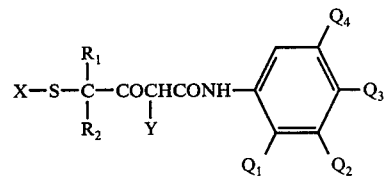

wherein X represents an alkyl group having 1 to 20 carbon atoms; Y represents a hydrogen atom or a group capable of being released on coupling with the oxidation product of a primary aromatic amine developing agent; $R_1$ and $R_2$, which may be the same or different, each represents an alkyl group having 1 to 6 carbon atoms; $Q_1$ represents a halogen atom, an alkyl group, an alkoxy group, an aryloxy group or an N-substituted amino group; $Q_2$, $Q_3$ and $Q_4$, which may be the same or different, each represents a hydrogen atom, a halogen atom, an alkyl group, an alkoxy group, an aryl group, an aryloxy group, an alkoxycarbonyl group, a carbamoyl group, a sulfamoyl group, an alkylamino group, an arylamino group, a sulfoamino group, an acylamino group, a carboxy group, a sulfo group, a cyano group or a hydroxy group.

2. The photographic silver halide emulsion as claimed in claim 1 wherein $Q_1$ represents a halogen atom or an alkoxy group, $Q_2$ and $Q_3$ each represents a hydrogen atom and $Q_4$ represents a hydrogen atom, an alkoxycarbonyl group, a carbamoyl group, a sulfamoyl group, a sulfoamimo group or an acylamino group.

3. The photographic silver halide emulsion as claimed in claim 2 wherein $Q_1$ represents a chlorine atom or a methoxy group.

4. The photographic silver halide emulsion as claimed in claim 1 wherein said alkyl groups for X, $R_1$ and $R_2$ are each unsubstituted alkyl groups.

5. The photographic silver halide emulsion as claimed in claim 1 wherein X represents an ethyl group.

6. The photographic silver halide emulsion as claimed in claim 1 wherein $R_1$ and $R_2$ each represents a methyl group.

7. The photographic silver halide emulsion as claimed in claim 1 wherein said coupler is α-(5,5-Dimethyl-3-hydantoinyl)-α-(2-ethylthio-2-methylpropionyl)-2'-chloro-5'-[4-(2,4-di-tert-amylphenoxy)butyramido]acetanilide, α-(5,5-Dimethyl-2,4-dioxo-3-oxazolidinyl)-α-(2-ethylthio-2-methylpropionyl)-2'-chloro-5'-[4-(2,4-di-tert-amylphenoxy)butyramido] acetanilide, α-(5,5-Dimethyl-2,4-dioxo-3-oxazolidinyl)-α-(2-ethylthio-2-methylpropionyl)-2'-methoxy-5'-[4-(2,4-di-tert-amylphenoxy)-butyramido]acetanilide, α-(1-Methyl-5-methoxy-3-hydantoinyl)-α-(2-ethylthio-2-methylpropionyl)-2'-methoxy-5'-[4-(2,4-di-tert-amylphenoxy)butyramide]acetanilide or α-(1-Benzyl-5-methoxy-3-hydantoinyl)-α-(2-ethylthio-2-methylpropionyl)-2'-methoxy-5'-[4-(2,4-di-tert-amylphenoxy)-butyramido]acetanilide.

8. The photographic silver halide emulsion as claimed in claim 1 wherein said coupler is α-(4-Carboxyphenoxy)-α-(2-n-octylthio-2-methylpropionyl)-2'-methoxyacetanilide.

9. A photographic light-sensitive material comprising a support having thereon the silver halide emulsion layer as claimed in claim 1.

* * * * *